(12) United States Patent
Park et al.

(10) Patent No.: US 9,081,003 B2
(45) Date of Patent: Jul. 14, 2015

(54) SYSTEMS AND METHODS FOR TESTING DRUGS AND DRUG DELIVERY SYSTEMS

(71) Applicant: Purdue Research Foundation, West Lafayette, IN (US)

(72) Inventors: Kinam Park, West Lafayette, IN (US); Bumsoo Han, West Lafayette, IN (US); Bongseop Kwak, Daegu (KR); Crystal Soo Jung Shin, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 119 days.

(21) Appl. No.: 13/886,810

(22) Filed: May 3, 2013

(65) Prior Publication Data

US 2013/0295601 A1    Nov. 7, 2013

Related U.S. Application Data

(60) Provisional application No. 61/642,308, filed on May 3, 2012, provisional application No. 61/798,610, filed on Mar. 15, 2013.

(51) Int. Cl.
*G01N 33/50* (2006.01)
*C12M 3/00* (2006.01)
*C12M 1/12* (2006.01)
*B01L 3/00* (2006.01)

(52) U.S. Cl.
CPC ........... *G01N 33/5011* (2013.01); *C12M 21/08* (2013.01); *G01N 33/5026* (2013.01); *G01N 33/5088* (2013.01); *G01N 33/5091* (2013.01); *B01L 3/5027* (2013.01); *B01L 2300/0877* (2013.01); *B01L 2300/0887* (2013.01); *B01L 2300/163* (2013.01); *C12M 25/04* (2013.01)

(58) Field of Classification Search
None
See application file for complete search history.

(56) References Cited

U.S. PATENT DOCUMENTS

| 5,750,329 | A  | * | 5/1998 | Quinn et al. | 435/1.1 |
|---|---|---|---|---|---|
| 6,368,562 | B1 |   | 4/2002 | Yao | |
| 7,763,456 | B2 |   | 7/2010 | Li et al. | |
| 8,355,876 | B2 |   | 1/2013 | Prabhakarpandian et al. | |
| 8,417,465 | B2 |   | 4/2013 | Prabhakarpandian et al. | |
| 8,647,861 | B2 | * | 2/2014 | Ingber et al. | 435/289.1 |
| 2004/0053422 | A1 | * | 3/2004 | Chan et al. | 436/180 |
| 2007/0102362 | A1 | * | 5/2007 | Iida et al. | 210/656 |
| 2007/0231887 | A1 | * | 10/2007 | McGrath et al. | 435/297.1 |
| 2013/0203086 | A1 | * | 8/2013 | Achyuta et al. | 435/7.92 |
| 2015/0072413 | A1 | * | 3/2015 | Zenhausern et al. | 435/347 |

* cited by examiner

*Primary Examiner* — Jill Warden
*Assistant Examiner* — Timothy G Kingan
(74) *Attorney, Agent, or Firm* — Maginot, Moore & Beck, LLP

(57) ABSTRACT

A system is provided that simulates the in vivo micro-environment of three-dimensional cellular structures or bodies, such as tumors. The system simulates the pressure gradients and fluid flows of the vascular and lymphatic systems as well as the interstitial and capillary transport mechanisms between the 3D cellular structure and the vascular and lymphatic systems. The system can be used to introduce drugs or drug delivery carriers to a tumor, for example, to assess the uptake capability and effect on the tumor. The system maintains the viability of the tumor cells for a sufficiently long period of time to permit testing of several different drugs and/or delivery carriers.

14 Claims, 12 Drawing Sheets

Step 1. Top layer fabrication processes

Photoresist spin coating on silicon wafer (SU-8 100, 2500rpm, 30sec, 100μm)

UV exposure and develop

PDMS microchannel fabrication for Top layer

Step 2. Bottom layer fabrication process

Photoresist spin coating on silicon wafer (SU-8 100, 2500rpm, 30sec, 100μm)

UV exposure and develop

PDMS microchannel fabrication for Bottom layer

SYSTEMS AND METHODS FOR TESTING DRUGS AND DRUG DELIVERY SYSTEMS

PRIORITY CLAIM

This application is a utility filing from and claims priority to provisional application No. 61/642,308, filed on May 3, 2012, and entitled "Biomimetric Microfluidic Platform for Testing Targeted Drug Delivery to Tumors", the entire disclosure of which is incorporated herein by reference, and to provisional application No. 61/798,610, filed on Mar. 15, 2013, and entitled "Biomimetric Microfluidic Platform for Testing Targeted Drug Delivery to Tumors", the entire disclosure of which is incorporated herein by reference.

This invention was made with government support under R01 EB 008388 awarded by National Institutes of Health and under CBET-1009465 awarded by National Science Foundation. The government has certain rights in the invention.

TECHNICAL FIELD

The present disclosure generally relates to systems and methods for testing targeted drug delivery to cellular structures, such as tumors. The present disclosure further relates to fluidic or microfluidic systems for such testing.

BACKGROUND

Developing and testing cancer drugs is an expensive process that typically involves exhaustive in vivo animal experiments. These experiments assist in analyzing how a drug is transported and delivered to its target in a tumor mass. However animal testing is a slow process and raises ethical concerns.

One recent alternative to animal testing involves the use of microfluidic systems to study the response of tumor cells to treatment protocols. Current microfluidic systems are based on two-dimensional platforms and thus inadequate to fully evaluate the response of a three-dimensional tumor mass.

Targeted drug delivery to tumors is an important challenge to be addressed in order to achieve effective cancer treatment without the toxic side effects of anti-cancer drugs. The ultimate objective of targeted drug delivery is to deliver most of the administered drug to the target, while eliminating or minimizing the accumulation of the drug at any non-target sites. Although many novel therapeutic agents have been developed for cancer treatments including chemotherapeutic agents, antiangiogenic agents, immunotoxins, and small interfering RNA (siRNA), their in vivo efficacy is still relatively poor. The recent development of nanotechnology provides a wide variety of nanostructures, whose properties can be tailored for targeted delivery to a certain extent. These nanostructures include liposomes, polymer micelles, dendrimers, drug nanocrystals, magnetic nanoparticles, gold nanoparticles/nanoshells, nanorods, nanotubes, and drug-polymer conjugates (all of which will be collectively referred to as NPs). Research aiming to precisely control the size and surface properties of these NPs to achieve targeted delivery is ongoing.

Currently these NPs are primarily designed based on so-called "passive" and/or "active" targeting strategies, which rely on extravasation and ligand-receptor interactions, respectively. Passive targeting is based on the physiological observation that tumor vasculature is leakier than normal vasculature. Since the tumor vasculature wall has larger pores (ranging from about 400-600 nm up to 2 μm in diameter obtained from xenograft models) compared to the normal case (typically smaller than 20 nm), the NPs (whose size is in between these cutoff pore sizes and whose surface is PEGylated for prolonged blood circulation) are believed to selectively accumulate at the tumor. The drug accumulation by the difference in this vascular permeability is often called the enhanced permeation and retention (EPR) effect and has been a key rationale to design NPs for targeted delivery.

Active targeting is a strategy to attach ligands on the surface of NPs so that the NPs selectively bind to the target tumor cells or endothelium. Clearly, active targeting occurs only after passive targeting. These strategies result in the improved accumulation of NPs at the tumor, but the in vivo efficacy of NPs and NP-mediated drugs is still significantly impaired. Only about 5% of the administered dose ends up at the target tumors. The remaining significant portion of the NPs is taken up by the reticulo-endothelial system (RES) of the spleen, liver, and lungs. In order to precisely control the transport of the majority of the administered NPs to target tumors, a new paradigm is needed that considers the complexity of their transport processes in vivo beyond the EPR effect.

One of the critical bottlenecks to developing new targeted delivery strategies is a limited quantitative understanding of the in vivo transport behavior of NPs due to a lack of versatile models to systematically study the in vivo transport characteristics. After being administered to a patient's blood stream, the NPs are thought to experience multiple levels of complex transport processes to reach the cancer cells. These processes include blood flow driven transport of the NPs, NP/endothelium interactions, extravasation, interstitial transport and cellular uptake. Because of the leaky vasculature of the tumor, as illustrated in FIG. 1, the NPs are thought to extravasate more in tumor vasculature than in normal vasculature. At the same time, however, the increased interstitial fluid, less functional lymphatic vessels, dense ECM microstructure and high cell packing density of the tumor may result in significantly elevated IFP, which can adversely affect the extravasation and interstitial transport of the NPs. In addition to the elevated IFP, the dense ECM microstructure and high cell packing density can also impair the interstitial transport of the NPs. FIG. 1 illustrates the vascular and tissue structure relevant to fluid and NP transport of normal and tumor tissues. In normal tissue, the endothelium is tightly packed so that the cutoff pore size is small and very low interstitial fluid flow presents. This fluid flows to the lymphatics through the normal ECM, and the IFP minimally builds up. On the other hand, the endothelium of tumor tissue is leaky and has large pores, which leads to high interstitial fluid flow and more extravasation of the NPs. In conjunction with less functional lymphatics and the dense ECM, this increased interstitial fluid flow results in elevated IFP, which adversely affects the extravasation. The compounding effects of the elevated IFP, leaky vasculature and poor vascularization of the tumor are still unknown.

These tumor micro-environmental parameters are highly dynamic, interconnected and vary spatiotemporally [24, 25], and the compounding effects of all these physiological parameters on NP transport are not yet fully understood. The conventional static in vitro systems described above, including cell suspensions and cell monolayers, lack dynamic interactions of tumor micro-environments among the fluids, ECM, cells and NPs, and are therefore inadequate to fully study these complex in vivo transport processes. Xenograft models have been valuable platforms to characterize the in vivo behavior of the NPs. However, even xenograft models often fail to simulate human in vivo environments or to provide a mechanistic explanation of the in vivo behavior of NPs. This are due to: (i) the unknown scaling factors to extrapolate from animal models to human subjects; (ii) the mismatch between human cancer cells and mice matrix environments; (iii) the difficulties to simulate the heterogeneity of tumor micro-environmental parameters; and (iv) the inability to independently control these parameters in the model. Thus, a new model system is greatly desired, in which the tumor micro-environmental parameters can be systematically and independently controlled, but at the same time the dynamic interactions among the fluids, ECM, cells and NPs are maintained Therefore, there is a need to develop a novel platform to simulate a three-dimensional tumor vasculature system which imitates the complex transport processes inside a tumor, such as transvascular transport, interstitial transport, and cellular transmembrane transport. It would be highly desirable to be able to simulate these processes on a single device, improving repeatability and speed, while reducing use of animals in drug discovery. This novel platform can be used to improve delivery efficacy, particularly for NPs, and to reduce non-specific accumulation at non-targeted sites.

SUMMARY

In one aspect of the present disclosure a microfluidic system is provided which includes an incubating platform including a reservoir configured to enable culturing cells and providing nutrients. The incubating platform further includes a membrane disposed adjacent the reservoir and configured to resemble vascular wall and endothelium. The incubating platform also includes a top panel disposed adjacent the membrane and fluid flow thereon is configured to resemble blood flow in vasculature. The microfluidic system is configured to simulate: i) transvascular transport process of a tumor; ii) interstitial transport; and iii) cellular transmembrane transport on a single device. The microfluidic system is configured to improve repeatability and speed as compared to in vivo testing.

The present disclosure further contemplates systems and methods for simulating the three-dimensional (3D) in vivo tissue micro-environments, particularly of a 3D tumor body. The key physiological features relevant to NP transport in vivo include: (i) fluid flow-driven transport along the tumor vasculature; (ii) transvascular transport across the endothelium; (iii) interstitial transport through the tumor interstitium; (iv) cellular uptake of the NPs by tumor cells with cell-cell and cell-ECM adhesion; and (v) transport of excess NPs to the lymphatic vessels. The systems and methods disclosed herein capture all of these physiological features in a controllable platform.

In one aspect, a microfluidic platform includes a top channel adapted to simulate the capillary with endothelium. The endothelium is simulated by a monolayer of endothelial cells on a nano-porous membrane. Various NPs can be introduced along this capillary channel. The platform includes a bottom panel having a center channel adapted to simulate a 3D tumor microstructure (i.e., cells in 3D matrix). The bottom panel also includes two side channels simulating the lymphatic vessels. Fluid pressure and flow rates in each channel are controlled to simulate the micro-environment for the tumor body. The platform may incorporate viewing windows to permit interactive viewing, sensing and measurement of the tumor body within the reservoir. Nutrients may be introduced into the simulated micro-environment to culture the tumor cells over a duration that is significantly longer than prior systems methods—e.g., over one or more weeks rather than one day.

The device and methods disclosed herein simulate the 3D micro-environment of a cellular matrix, such as a tumor, thereby providing an important tool in evaluating the efficacy of targeted drug delivery carriers, such as NPs, or the efficacy of certain drugs on tumor cells. The system and incubating platform disclosed herein can be tailored to a particular test or cell type, such as by controlling fluid flow and pressure in the various channels or changing the membrane between the top and bottom panels to alter the endothelial transport capabilities. The system disclosed herein further allows accurate control of the pressure gradients within the reservoir containing the target tissue or tumor, which in turn can provide a more accurate simulation of the perfusion of drug delivery carrier into the target tissue/tumor.

It is thus contemplated that the systems and methods described herein can be used to evaluate targeted drugs and drug delivery carriers based on tissue samples from a patient. In particular, tissue obtained form a tumor biopsy of a patient can be engineered into a 3D cellular matrix that is placed within the system and incubating platform described herein. The system accurately emulates the micro-environment of the actual tumor so that the performance, uptake or activity of the drug, carrier or tumor cells themselves detected by the system will be an accurate indicator of the performance or activity of the drug, carrier or tumor cell in the patient.

Moreover, the targeted cells can be sustained for a much longer period of time than with prior systems and methods, on the order of about two weeks. The system described herein can introduce nutrients to the target 3D cellular matrix to keep the matrix or matrixes viable while different drug or drug delivery protocols are tested. The systems and methods described herein can be used for the testing of a variety of 3D cellular matrixes, including, but not limited to, tumors, fibroblasts and the like.

DETAILED DESCRIPTION

Figure 1:
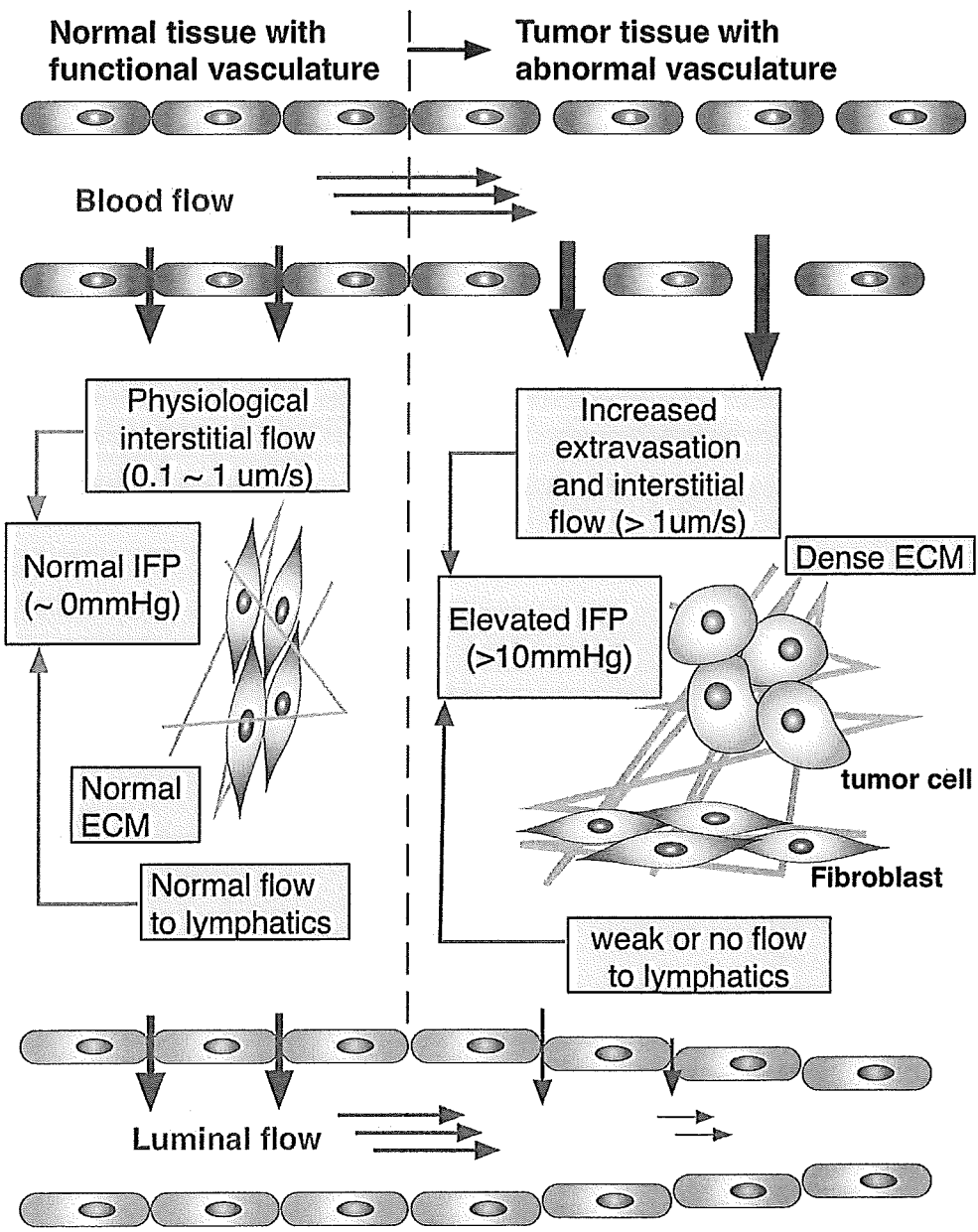
FIG. 1 is a representation of the vascular and tissue structure and the flow patterns for a tumor micro-environment.

For the purposes of promoting an understanding of the principles of the present disclosure, reference will now be made to the embodiments illustrated in the drawings, and specific language will be used to describe the same. It will nevertheless be understood that no limitation of the scope of this disclosure is thereby intended.

A novel fluidic system is described herein that is configured to simulate: i) transvascular transport process of a tumor; ii) interstitial transport; and iii) cellular transmembrane transport, all in a single platform or device. In one embodiment the fluidic system is a microfluidic system sized to analyze three-dimensional (3D) cell structures, such as tumor bodies. The system is further configured to improve repeatability and speed as compared to in vivo testing.

Figure 2:
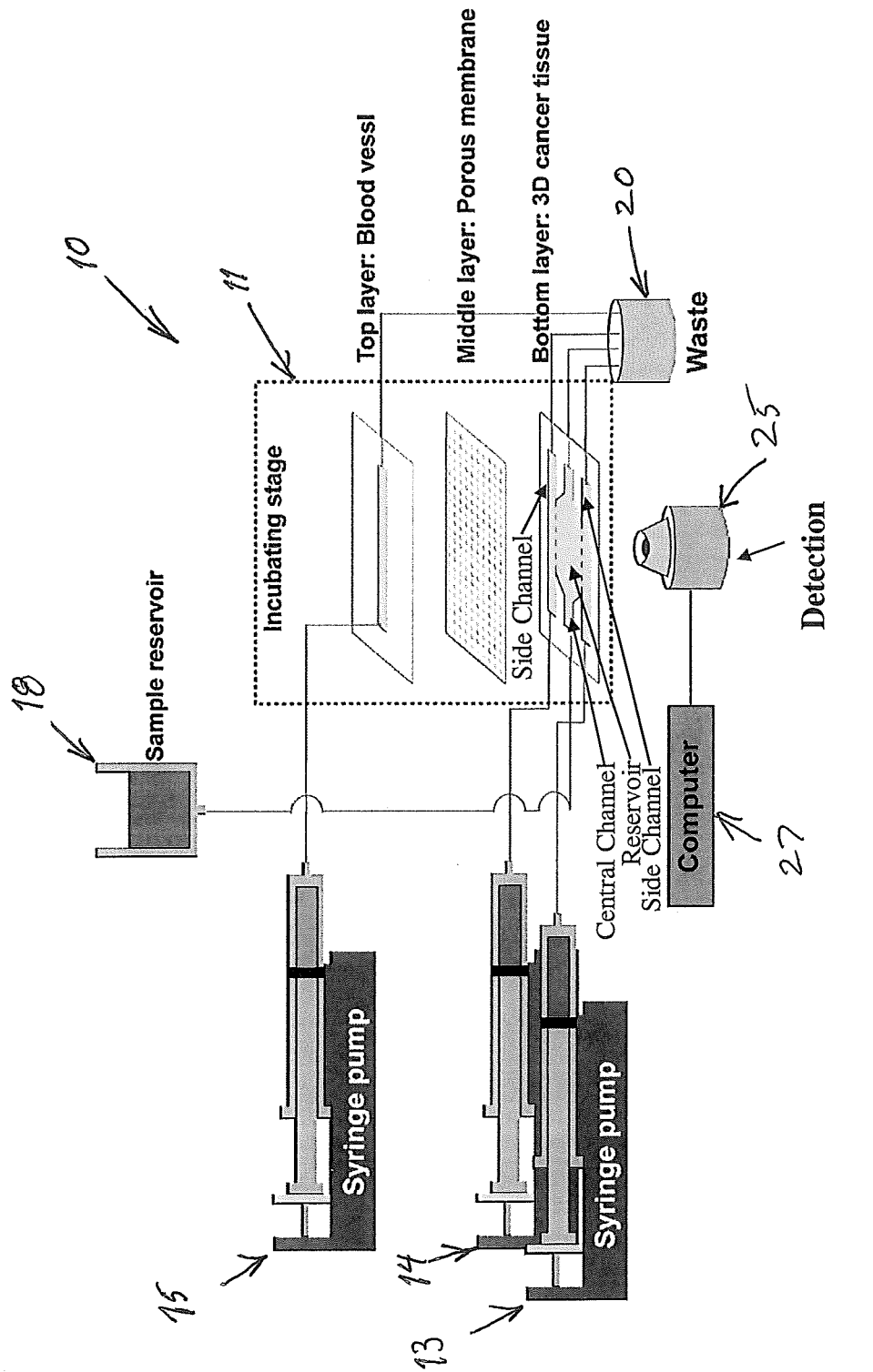
FIG. 2 is a schematic representation of a microfluidic system including an incubating platform depicted in an exploded view according to the present disclosure.

Referring to FIG. 2, a schematic is shown of a microfluidic system 10 that includes an incubating platform 11 depicted in an exploded view according. The system 10 includes input devices 13, 14, 15 that are configured to deliver a flow of fluid under pressure to channels defined in the incubating platform (as described in more detail herein). In one embodiment the input devices may be syringe pumps, although other manual, mechanical and electrical pumps are contemplated. In the embodiment depicted in FIG. 1, three input devices are utilized to deliver the various fluids; however, it is possible to utilize more or less input devices.

The system 10 also includes a sample reservoir 18 in fluid communication with a reservoir defined in the incubating platform (as described in more detail herein). In one embodiment the sample reservoir may incorporate a fluid column configured to maintain a predetermined pressure within the reservoir without fluid flow through the reservoir. The system further includes a waste reservoir 20 in fluid communication with the incubating platform to receive fluids and waste materials flushed from the incubating platform at the conclusion of a procedure. A detection unit 25 provided with the system that is configured to monitor the incubating platform and in particular the cellular activity within the reservoir. The detection unit may be a microscope or may be configured to generate electronic data that is provided to a computer 27 included in the system. The computer may be programmed to analyze the detection data as described in more detail herein.

Figure 3:
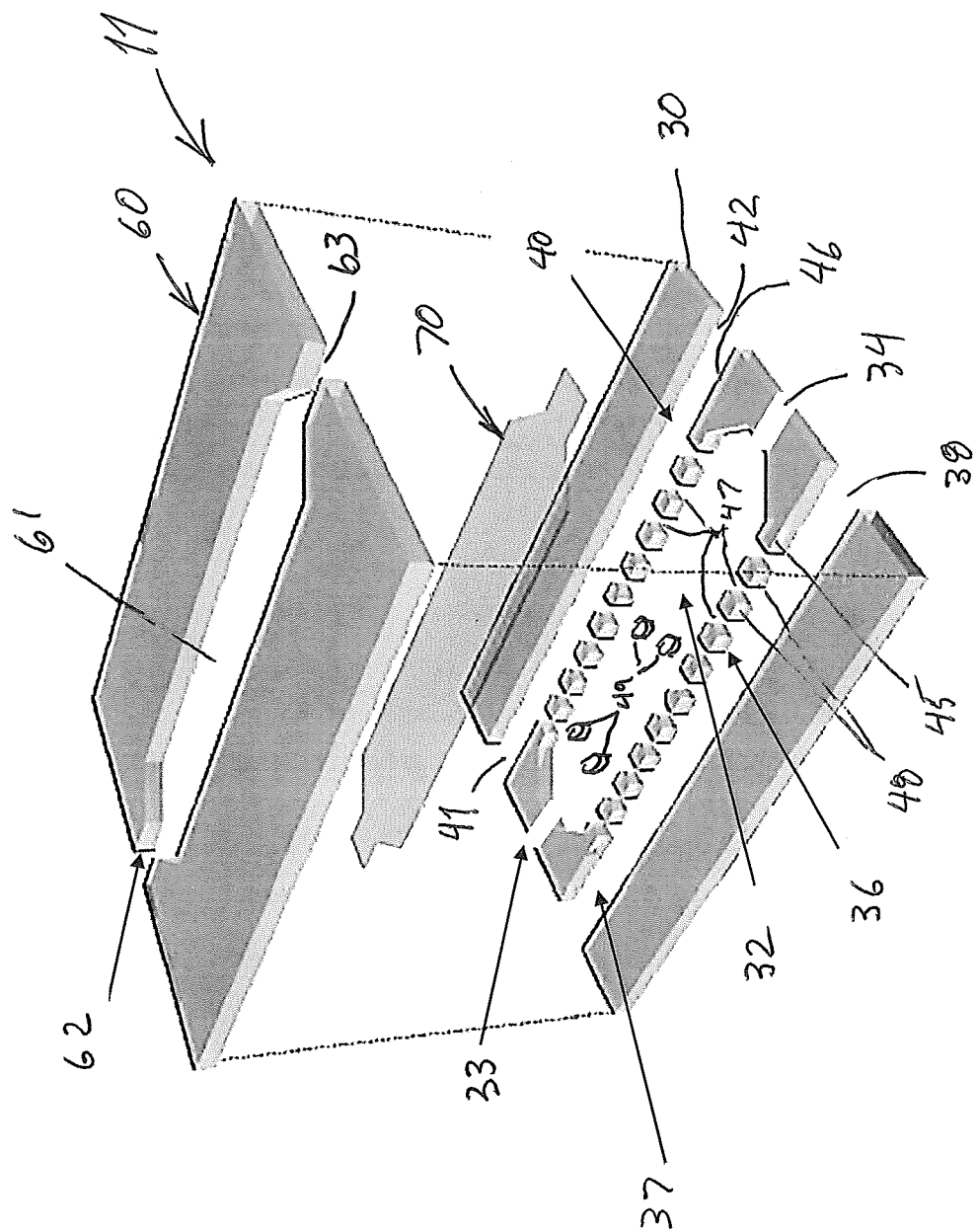
FIG. 3 is an exploded view of the incubating platform depicted in FIG. 2.
Figure 5:
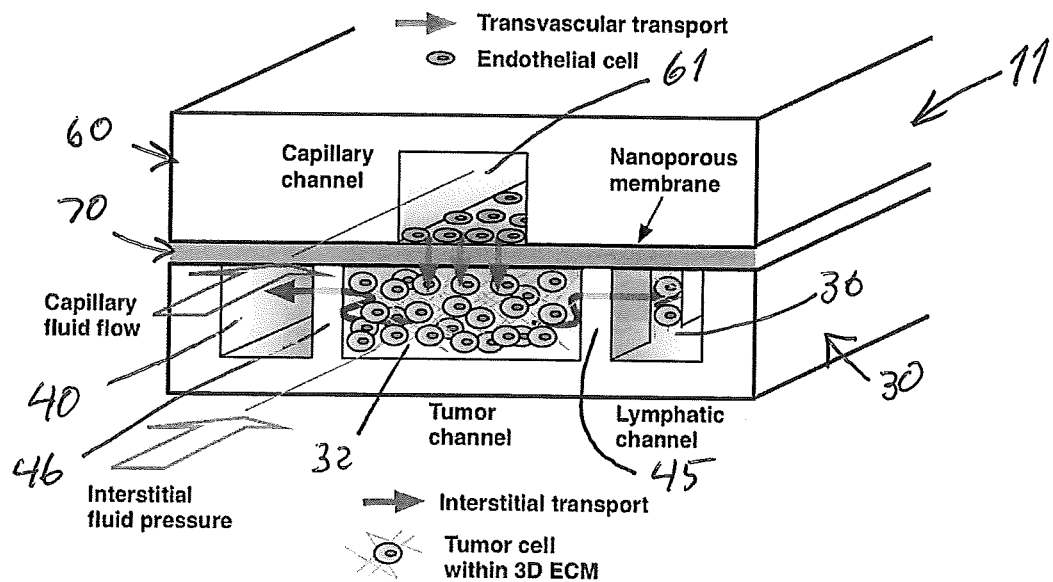
FIG. 5 is a representation of the incubating platform depicted in FIG. 3 showing fluid flow and transport flows.
Figure 4:
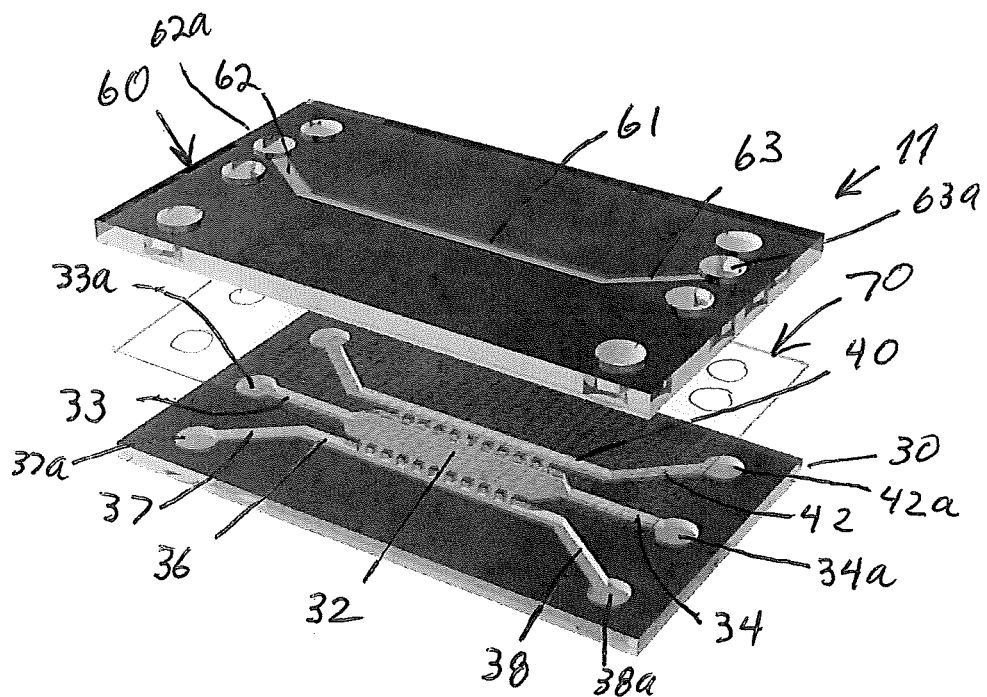
FIG. 4 is an exploded view of a modified incubating platform shown in FIG. 2.

The incubating platform 11 is configured to support a 3D cellular structure or matrix for testing and evaluation, such as a biopsy specimen of a tumor, rather than the 2D and single cell samples evaluated in prior systems. Details of the structure of the incubating platform are shown in FIGS. 3-5. The platform 11 includes a bottom panel 30 which is configured to enable culturing cells and 3D cell structures, and for providing nutrients and nano-particles (NPs), such as the NPs described above, to the cellular matrixes. The bottom panel 30 defines a reservoir 32 that is sized to contain multiple 3D cellular structures or matrixes, such as tumor specimens. The reservoir 32 is in fluid communication with an inlet channel 33 and an outlet channel 34 defined at opposite ends of the reservoir. As shown in FIG. 4, the channels 33, 34 terminate in corresponding fluid interfaces 33a, 34a that are configured for fluid engagement to a fluid conduit. In particular, the fluid interface 33a at the inlet channel 33 is configured for fluid connection to the sample reservoir 18, while the interface 34a at the outlet channel 34 may be in fluid connection with the waste reservoir 20. Alternatively, the inlet and outlet channels may be in fluid connection with fluid columns configured to maintain a predetermined and controllable fluid pressure within the reservoir 32.

In a further aspect of the incubating platform 11, the bottom panel 30 defines at least one side channel, such as the channels 36, 40 shown in FIGS. 3-5. The two channels flank the reservoir 32 and preferably are coincident with the length of the reservoir. The channels may be wide, as depicted in FIG. 3, or may be more narrow conduits, as depicted in FIG. 4. The channels 36, 40 include corresponding inlet channels 37, 41 and outlet channels 38, 42, each with their own respective fluid interface 37a, 38a, 41a, 42a, as shown in FIG. 4. The interfaces 37a, 41a at the inlet channels 37, 41 of the two side channels 36, 40 are configured for fluid connection to the input devices 13, 14 described above. The interfaces 38a, 42a the outlet channels 38, 42 of the two side channels may be in fluid connection with the waste reservoir 20. Alternatively, the outlet interfaces may be fluidly connected to an input device similar to the input devises 13, 14. In the embodiment depicted in FIG. 1, two side channels are depicted adjacent the reservoir.

In one feature of the incubating platform 11, the reservoir is in fluid communication with the side channel(s) in a manner that allows nutrients and NPs to pass from the side channels into the reservoir, while preventing passage of the cultured cells/tumor tissue contained within the reservoir. Thus, in one embodiment, a wall 45 separates the side channel 36 from the reservoir 32 and a wall 46 separates the opposite side channel 40 from the reservoir. Both walls define a plurality of openings 47 therethrough that are sized to prevent egress of the 3D cellular matrix but are sufficiently large to permit passage of nutrients and NPs from the side channels into the reservoir. In one specific embodiment the openings are formed by a series of posts 48 that are spaced apart by a predetermined distance. Additional posts 49 may be formed in the interior of the reservoir, as shown in FIG. 3. These posts are provided for structural support of the top panel and membrane, described below.

The incubating platform 11 further includes a top panel 60 overlaying the bottom panel 30. The top panel defines a top channel 61 that is aligned with the reservoir 32 and is generally coextensive with at least the length of the reservoir as shown in FIGS. 3-4. In one embodiment shown in FIG. 3, the top channel 61 is similarly configured to the reservoir 30. In another embodiment shown in FIG. 4 the top channel is configured as a narrower conduit, similar to the side channels 36, 40. The top channel includes an inlet channel 62 that is fluidly coupled to an input device and configured to receive a fluid therefrom. The top channel further includes an outlet channel 63 that may be fluidly connected to the waste reservoir or to another input device. The inlet and outlet channels include respective fluid interfaces 62a, 63a for providing the fluid connection to the input devices and/or waste reservoir.

With respect to the width of the side channels 36, 40 and the top channel 61, it can be understood that one aspect of the microfluidic system 10 and in particular incubating platform 11 is to simulate the micro-environment of the 3D cell structure, and more particularly the micro-environment of a tumor. As explained above and as illustrated in FIG. 1, the tumor environment includes vascular flow and luminal flow through lymphatic vessels, together with interstitial flow between the blood and lymphatic vessels and the tumor body. The side channels 36, 40 are thus configured to simulate the lymphatic vessels, as well as the lymphatic fluid flow and pressures. Similarly, the top channel 61 is configured to simulate the blood vessels as well as the vascular flow and pressures. Thus, the channels are preferably sized to enhance this simulation. Moreover, the channels are preferably sized commensurate with the size of the reservoir, which is configured to simulate the 3D tumor body itself. In a specific embodiment, the top channel 61 is 300 µm an wide and 50 µm an high, the reservoir is 900 µm×100 µm an (w×h) and the two side channels 36, 40 are 300 µm wide by 100 µm an high. The tumor and lymphatic channels are separated with a series of 100 µm×100 µm an posts 36 separated by 100 µm, with six posts 49 in the tumor reservoir to minimize the contraction or movement of the tumor tissue during culture and experiments.

To further simulate the 3D micro-environment, the incubating platform further includes a membrane 70 disposed between the top and bottom panels and more particularly between the reservoir 32 and the top channel 61. The membrane may be configured similar to the reservoir and channel, as shown in FIG. 3, or may be a sheet that is generally coincident with the panels, as shown in FIG. 4. The membrane 70 is configured to resemble the vascular wall in its porosity Thus, for the incubating platform described herein which is adapted to accommodate tumor bodies, the membrane is a nano-porous membrane. The pore sizes may range from 100 nm to 1000 nm and the pore area for the membrane may range from 5% to 15%. The membrane 70 is thus configured to permit transport of nutrients and NPs into the reservoir 32 and to prevent passage of the 3D cellular structures from the reservoir into the top channel. In certain embodiments, the membrane can be formed from a layer of PDMS or a polycarbonate treated to form the nanometer sized pores. To further simulate the tumor micro-environment, the membrane 70 is coated with endothelial cells on the surface disposed within the top channel 61. The endothelial cells thus enhance the simulation of the capillary flow between the top cannel 61, which simulates a blood vessel, and the reservoir 32, which simulates the 3D tumor body.

Figure 6:
FIG. 6 is a schematic representation of steps in the fabrication of the incubating platform shown in the prior figures.
Figure 6:
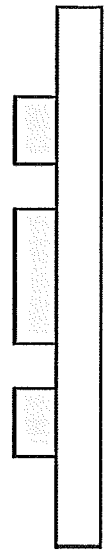
Figure 6:
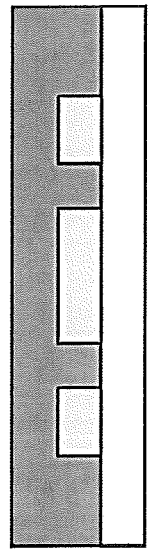
Figure 6:
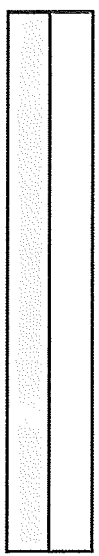
Figure 6:
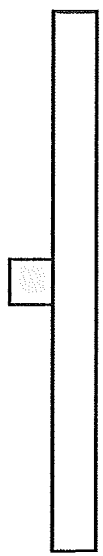
Figure 6:
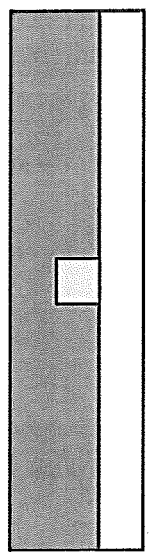
Figure 7:
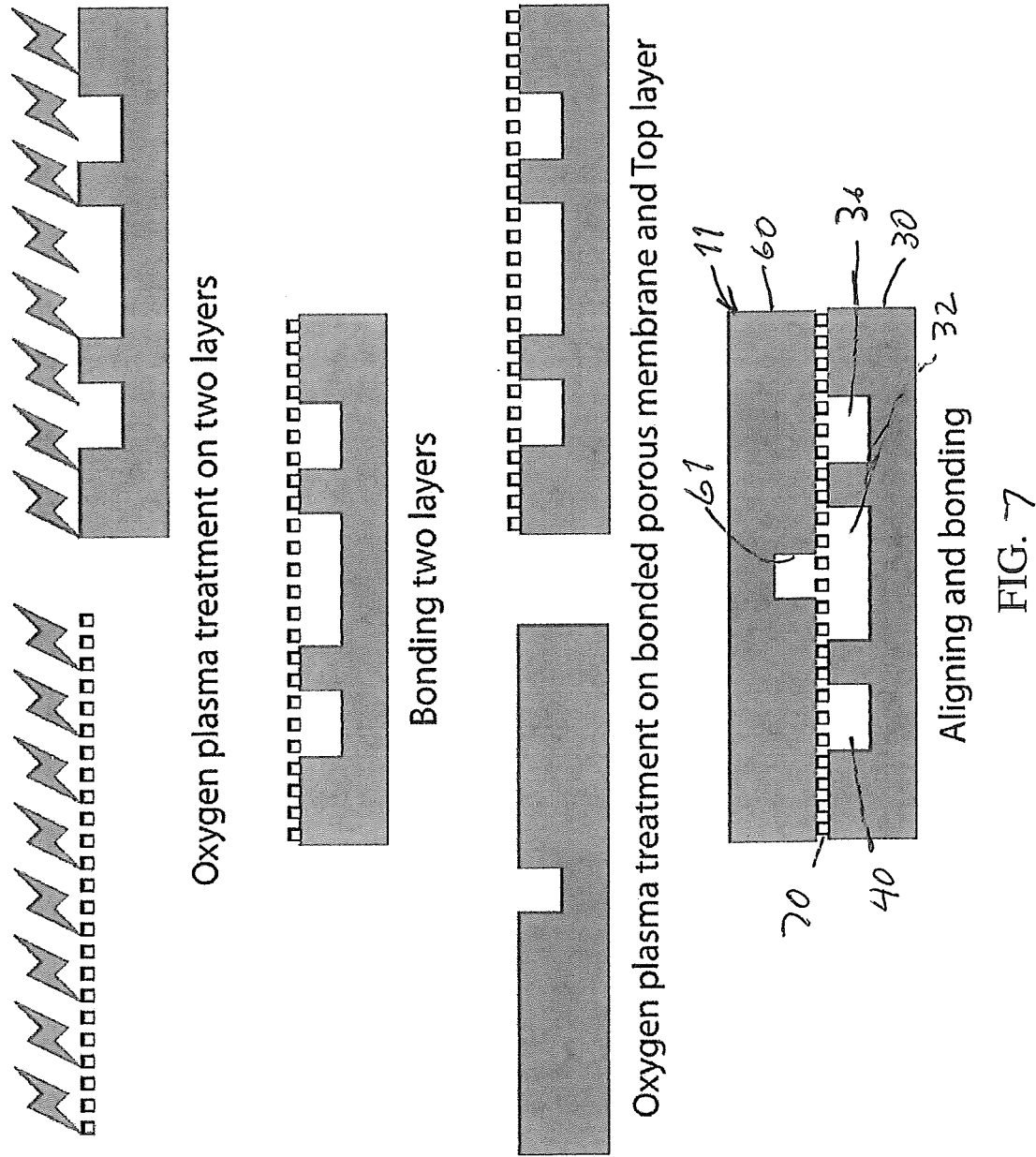
FIG. 7 is a schematic representation of further steps in the fabrication of the incubating platform shown in the prior figures.
Figure 8:
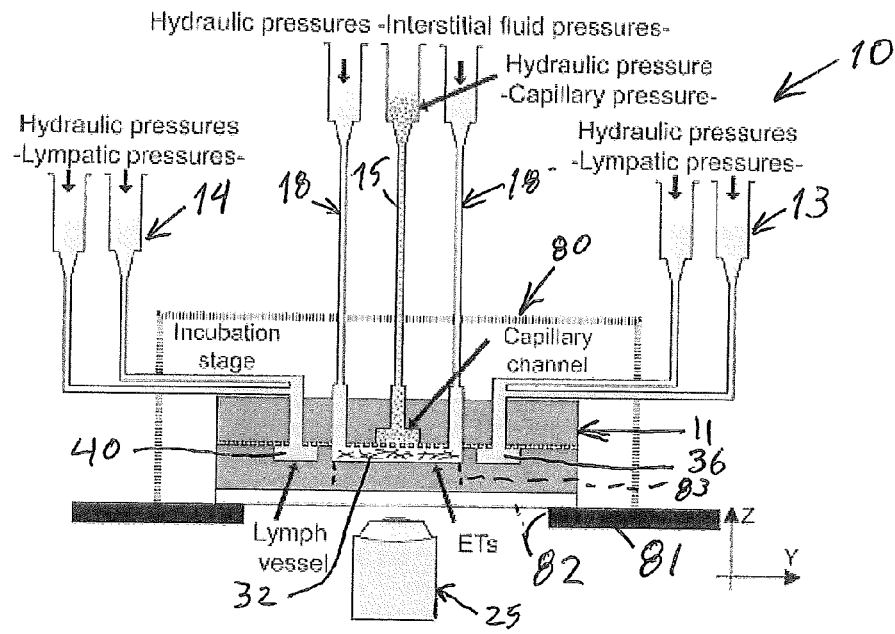
FIG. 8 is a schematic representation of the microfluidic system shown in FIG. 1.

The bottom and top panels can be made from Polydimethylsiloxane (PDMS) or other polymeric substrates formed on a hard substrate such as silicon. The patterns for the reservoir, the top channel, and the side channel(s) can be formed in the respective panels 30, 60 by a photolithography technique, which incorporate spin coating photoresist on a silicon wafer, etching the photoresist layer to form the channel/reservoir molds, and then molding the PDMS on the etched wafer, as depicted in FIG. 6. Then, the panels and the membrane are subjected to oxygen plasma treatment and then bonded together with the membrane 70 sandwiched between the panels to form the completed incubating platform 11, as depicted in FIG. 7. IN a specific example, the incubating platform is fabricated by providing an SU-8 photoresist spin-coated on silicon dioxide (SiO2) wafers, and then baking the wafers. The wafers are then exposed to UV light through a mask with channel configurations. After the post-baking procedure, the wafers were immersed into an SU-8 developer solution and rinsed with isopropyl alcohol. Then, a mixture of polydimethylsiloxane (PDMS) and curing agent is poured on the silicon wafer (i.e., the mold) and baked. After polymerization, the PDMS layers are peeled off from the mold. The PDMS layers are cleaned, and the inlet and outlet ports were punched into the wafer. A polycarbonate membrane with 400 nm pores (Cyclopore, Whatman), treated with 3-aminopropyltriethoxysilane solution, can be added, dried, and then bonded between the top and bottom PDMS layers.

To further expand on the system illustrated in FIG. 2, the system 10 can be mounted within a housing or fixture 80, and in particular supported on a plate 81. The plate defined aperture 82 that is aligned with the reservoir 32 so that the detection device 25 has a direct view of the reservoir. The bottom panel 30 may thus incorporate a viewing window 83 defined therein beneath the reservoir 32. The detection device monitors the incubation process of the 3D cellular matrixes within the reservoir as well as the activity of the endothelial cell layer on the membrane 70. The detection device can be calibrated to distinguish healthy/growing cells from unhealthy dead cells as an avenue for assessing drug efficacy. The detection device can also be configured to assess the efficacy of certain targeted drug delivery carriers, such as NPs.

As explained above, the incubating platform 11 is configured to simulate the micro-environment of a 3D tumor body. As depicted in FIG. 5, the incubating platform 11 includes tumor cells within a 3D extracellular matrix (ECM) within the reservoir 32. The fluid within the reservoir is maintained at a predetermined interstitial pressure. The side channels 36, 40 are supplied with fluid to simulate the lymphatic system, and more particularly to allow the platform 11 to accurately simulate the interstitial transport between tumor body and lymphatic vessels. The top channel 61 is supplied with fluid at a pressure and flow rate to simulate capillary flow within a blood vessel, and more particularly to allow the platform to accurately simulate the transvascular transport between blood vessels and tumor bodies.

Thus, the side channels 36, 40 are supplied with a fluid under a pressure and flow rate designed to simulate the lymphatic pressure and flow. The fluid in the simulated lymphatic channels 36, 40 is supplied by the input devices 14, which are in the form of fluid pumps. Similarly, the fluid within the top channel is supplied at a pressure and a flow rate to simulate the vascular conditions by way of input device 15. The interstitial fluid pressure within the reservoir 32 can be maintained by input devices 18, which may be fluid columns at a predetermined pressure. By way of example, the simulated lymphatic pressure in the side channels can be about 5 mmHg, the simulated capillary pressure in the top channel can be in the range of 10-40 mmHg, and the simulated interstitial pressure in the reservoir can be in the range of about 5 to 150 mmHg.

Figure 9:
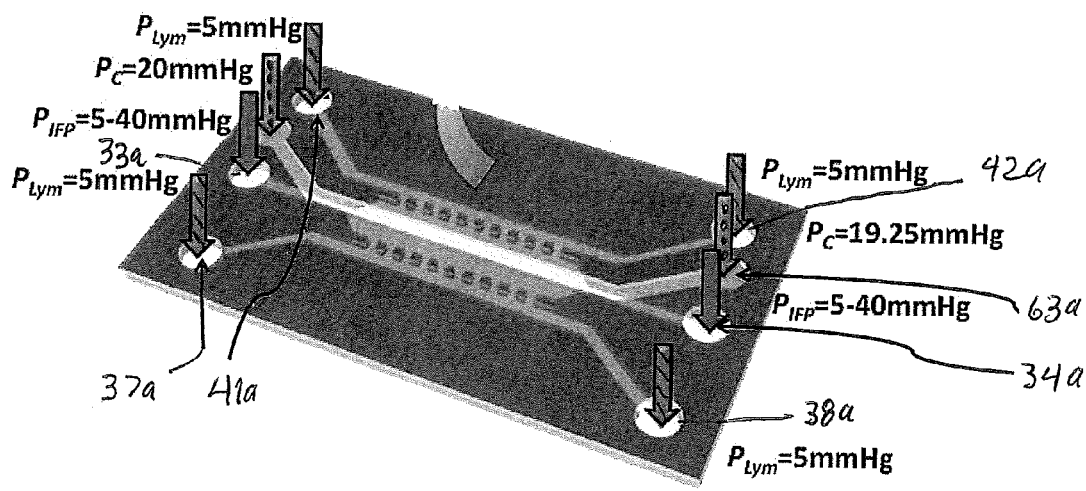
FIG. 9 is a top perspective view of the fluid flow paths of the platform shown in FIG. 2 with exemplary fluid pressures.

FIG. 9 represents the fluid pressures in one specific application of the system 10 for incubating and evaluating tumor cell growth. The lymphatic pressure applied to the side channels at the inlets 37a, 38a, 41a, 42a is 5 mmHg, the capillary pressure applied at the inlet 62a is 20 mmHg while at outlet 63a the pressure is 19.25 mmHg, and the interstitial fluid pressure applied at the inlets 62a, 63a is between 5 and 40 mmHg. In this example, the equal pressures at the inlet and outlet of the side (lymphatic) channels and in the reservoir means that there is no fluid flow through these channels. On the other hand, the pressure differential between the inlet and outlet of the top channel 61 generates a flow rate that is intended to simulate a typical vascular blood flow. It can be appreciated that these pressure values are exemplary and that the system 10 permits adjustment of the pressures as necessary to improve the simulation of the complex pressure balance in an in vivo 3D tumor micro-environment. In a preferred protocol, the interstitial channel, or reservoir 32 is pressurized first, followed by the lymphatic channels, or side channels 32, 40. The capillary channel, or top channel 61 is pressurized last.

Currently NPs are designed using the concept of the EPR effect (enhanced permeation and retention), which has been found to be suitable to explain the improved therapeutic effects of NPs as compared with conventional chemotherapy with low molecular weight drugs. However, the EPR effect does not explain the absolute accumulation of the NPs at the tumor. Instead, the NP transport to the tumor is a confounded result attributed to various in vivo transport mechanisms including the clearance by the reticulo-endothelial system (RES), the decreased extravasation by the elevated interstitial fluid pressure (IFP), and the hindered interstitial transport by the high IFP and dense ECM microstructure of the tumor. Nanoparticles must transport through the highly complex tumor micro-environment, whose biological, mechanical, and chemical conditions vary in a spatiotemporal manner. Development of truly targeted drug delivery systems requires design paradigms that overcome the limitations of the prior oversimplifications of the complex bio-transport phenomena. In addition to changes in strategies, new experimental methods and evaluation criteria for successful delivery are also required beyond the limitation of conventional in vitro cell culture models and in vivo xenograft models.

The incubating platform 11 and system 10 simulate the key physiological features relevant to NP transport in vivo, namely: (i) fluid flow-driven transport along the tumor vasculature; (ii) transvascular transport across the endothelium; (iii) interstitial transport through the tumor interstitium; (iv) cellular uptake of the NPs by tumor cells with cell-cell and cell-ECM adhesion; and (v) transport of excess NPs to the lymphatic vessels. In using the system 10 described herein, various NPs can be introduced into the capillary channel or the top channel 61 while the reservoir 61 retains the tumor specimens to the 3D tumor microstructure. The reservoir is pressurized to simulate the elevated IFP found in the tumor body micro-environment. The NP-suspended fluid will flow along the top channel at a physiologically relevant velocity and pressure.

Although it is not a tumor micro-environmental parameter, the clearance of the NPs via the RES is believed be critical to the outcome of the NP transport. This feature can be considered by decreasing the concentration of the NPs in the capillary channel 61 with respect to time by dilution. The concentration change can be calibrated based on information regarding the temporal concentration changes of NPs in the blood stream. The input devices 15 supplying the NP-suspended fluid flow through the top channel can be controlled to achieve this temporal NP concentration change.

Figure 10:
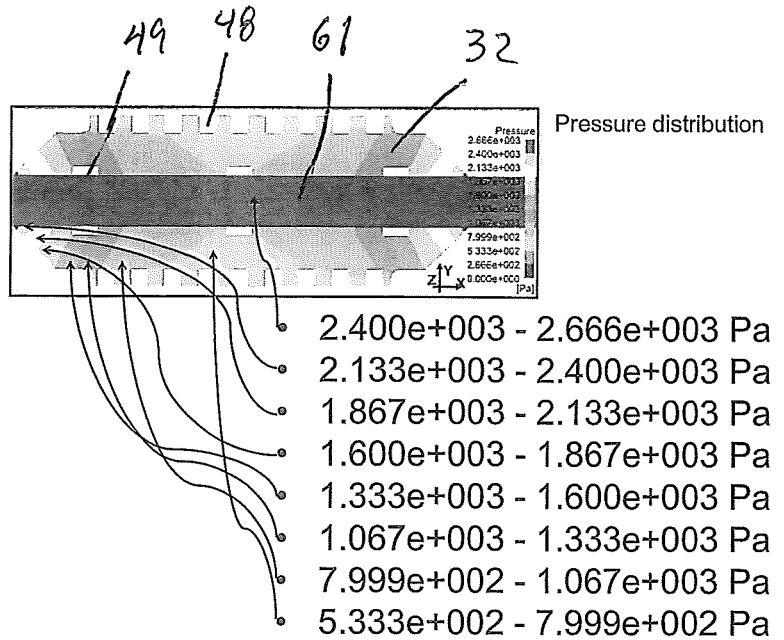
FIG. 10 is a graph of pressure distribution within the tumor reservoir of the incubating platform shown above.
Figure 11:
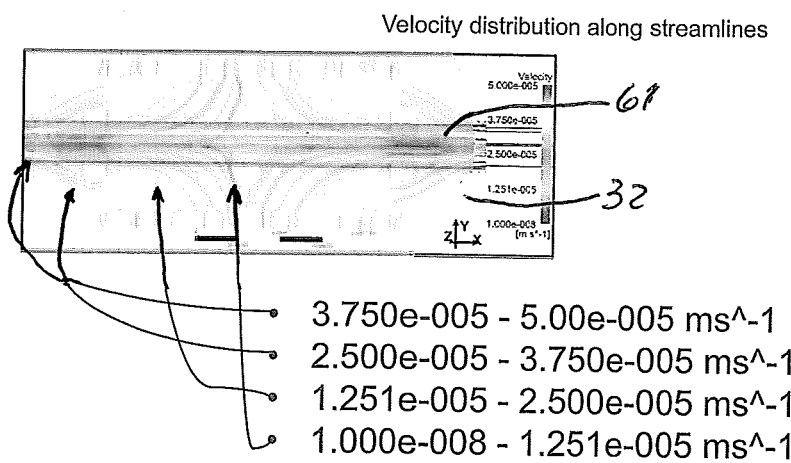
FIG. 11 is a graph of fluid velocity distribution within the tumor reservoir of the incubating platform shown above.
Figure 12:
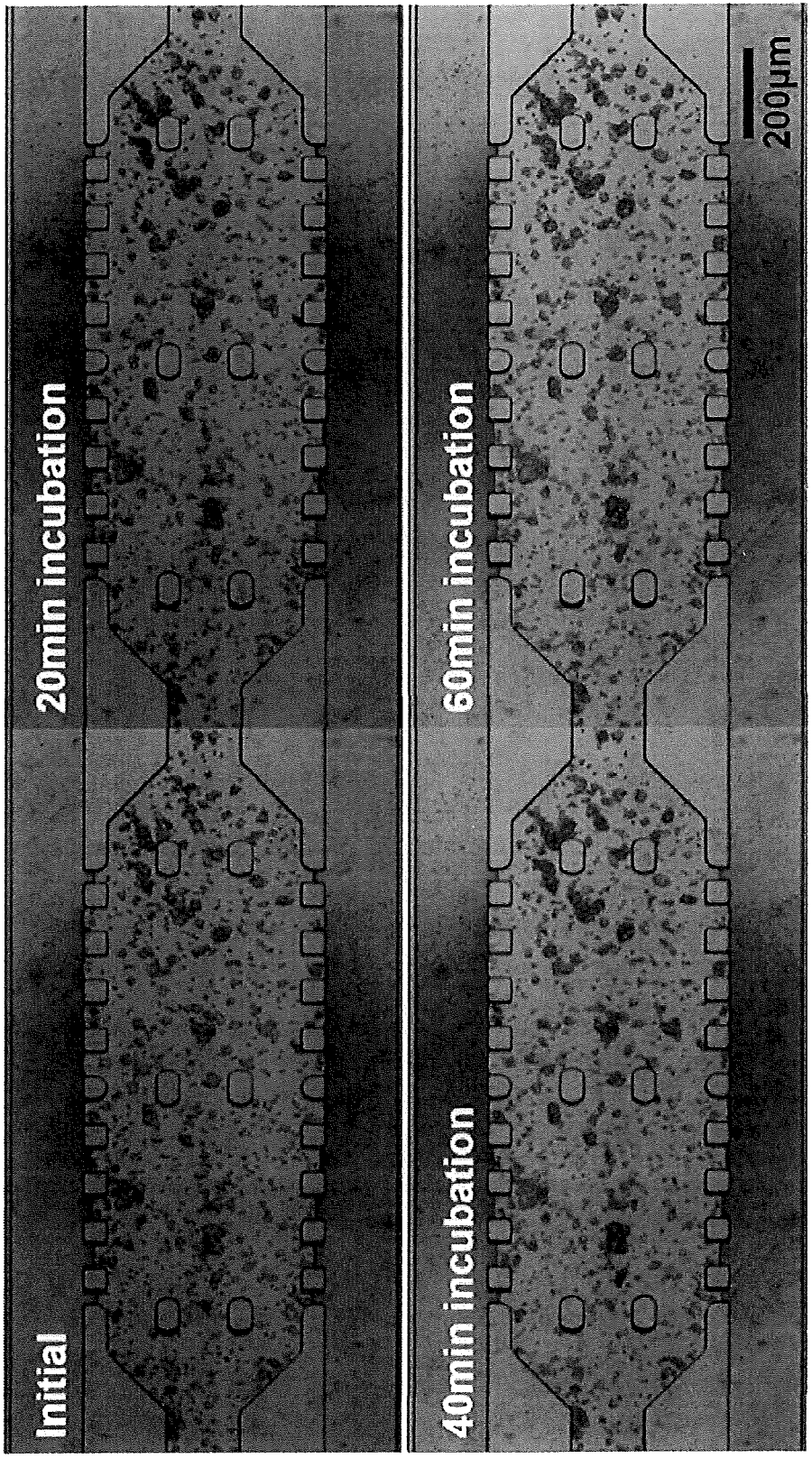
FIG. 12 depicts photographs of the incubating platform during an incubation process performed over a one-hour period.
Figure 13:
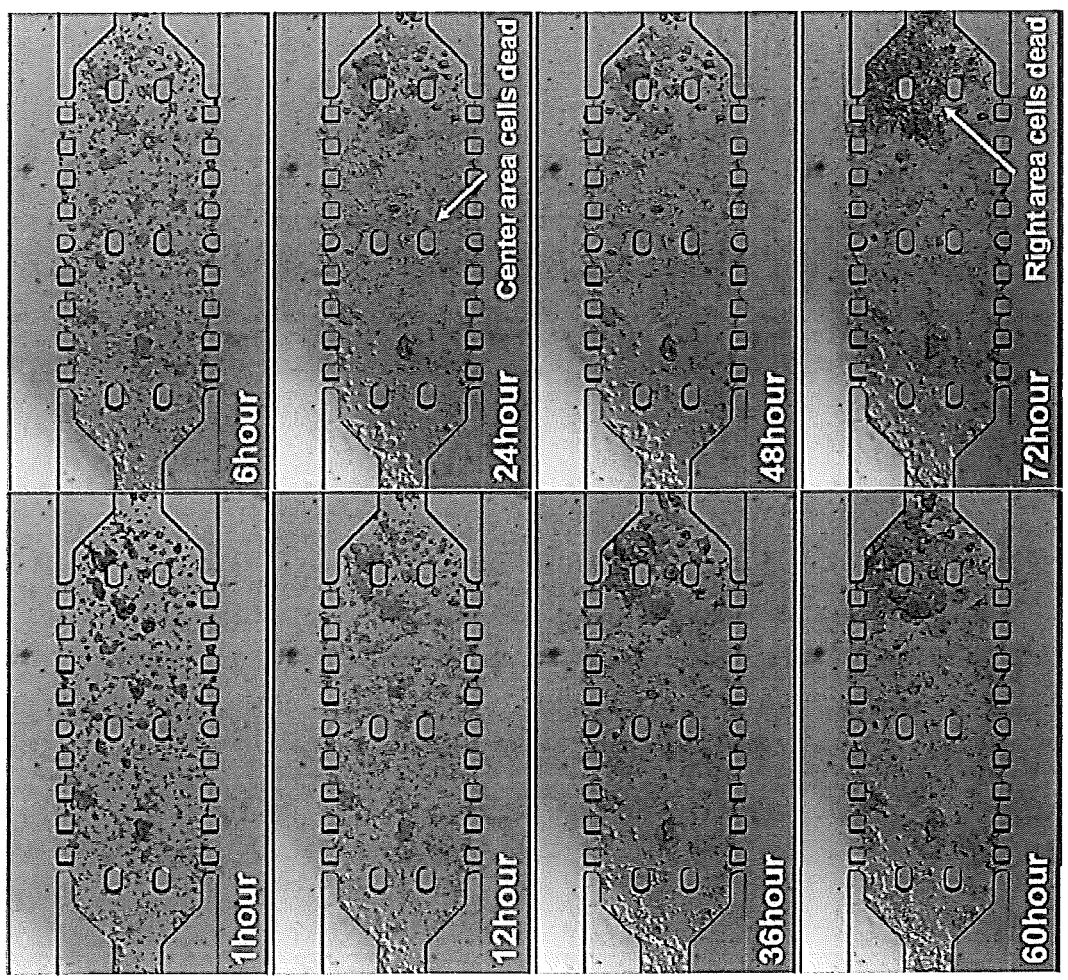
FIG. 13 depicts photographs of the incubating platform during a cell culturing process performed over a seventy-two hour period.
Figure 14:
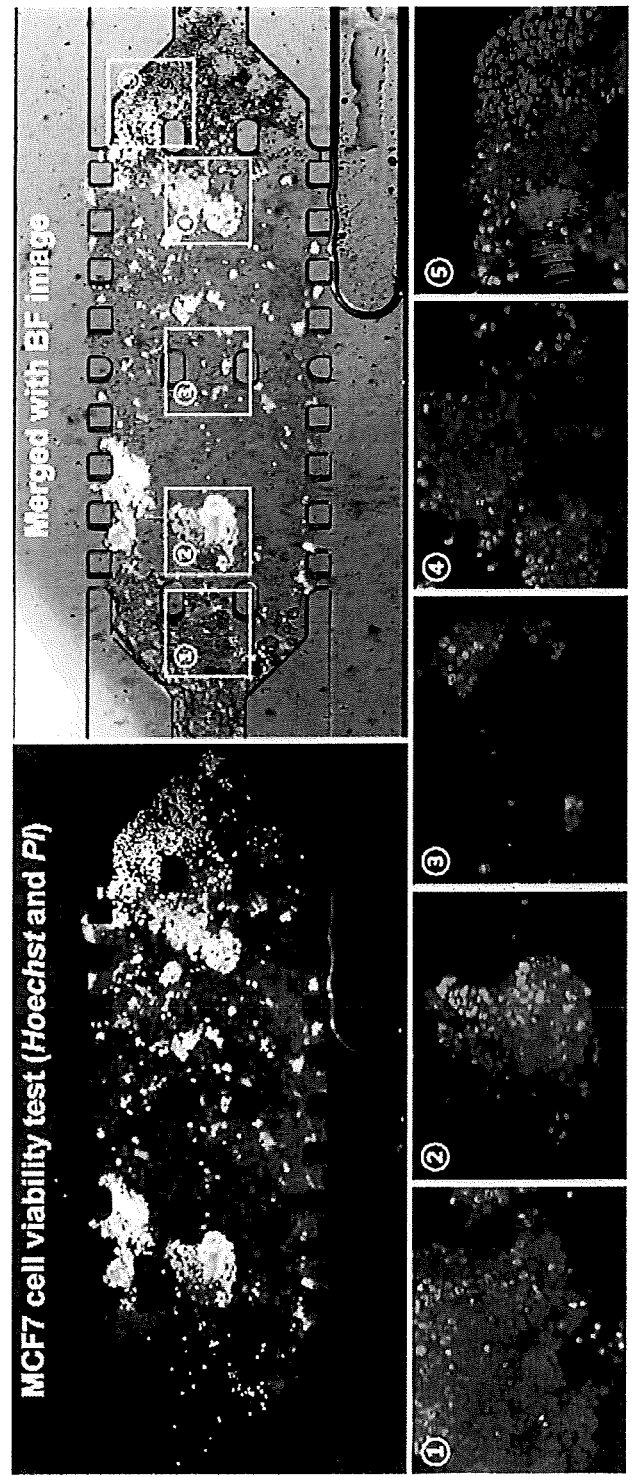
FIG. 14 depicts photographs representing viability of MCF7 cells cultured for three days on the microfluidic device. The MCF7 cells were stained with Hoechst (all cells) and Propidium Iodide (dead cells).

In the tumor reservoir 61, cancer cells can be incubated to grow within a 3D collagen matrix. Interstitial fluid flows through the matrix and exerts elevated IFP. The NPs will be transported through this 3D tissue structure and reach the cancer cells. The excess NPs and interstitial fluid will be collected in the two side lymphatic channels via the simulated interstitial transport through the openings 47 in the walls 45, 46 between the lymphatic side channels 36, 40 and the reservoir 61. The physical structure of the incubating platform 11, together with a protocol to control the channel pressures, allows the system 10 to accurately simulate the NP transport mechanism into tumors in vivo. Pressure distribution and velocity distribution graphs shown in FIGS. 10, 11 illustrate the effect of the controlled pressures in the platform 11 and confirm the presence of interstitial and lymphatic flows Incubation results for one experimental procedure are shown in FIG. 12. The incubation process was performed during a one-hour period. MCF7 cells were suspended in 3 mg/ml collagen solution, and introduced to the incubating platform 11. The collagen was polymerized and MCF7 cells grown in a 3DI extracellular matrix. After 1 hour incubation, the MCF7 cells in collagen matrix were further cultured for 72 hours. Meanwhile, the cell culturing media was supplied through both side channels 36, 40. The results of the 72-hours cell culturing are shown in FIG. 13. To demonstrate the cell viability after long-term culture, the cultured sample was stained with Hoechst (all cells) and Propidium Iodide (PI) (dead cells). A mixture of 10 μL of Hoechst solution and 20 μl of PI solution were added into 2 mL of culture medium. Then, the culture medium with staining solution continuously flows through side channels for 30 min. Next, a washing stage was performed with Dulbecco's Phosphate Buffered Saline (DPBS) for 30 min. FIG. 14 depicts fluorescence microphotographs showing the viability of MCF7 cells after three-day culture on the microfluidic system 10 disclosed herein. Some dead cells are observed, but the majority of cells are live.

Figure 15:
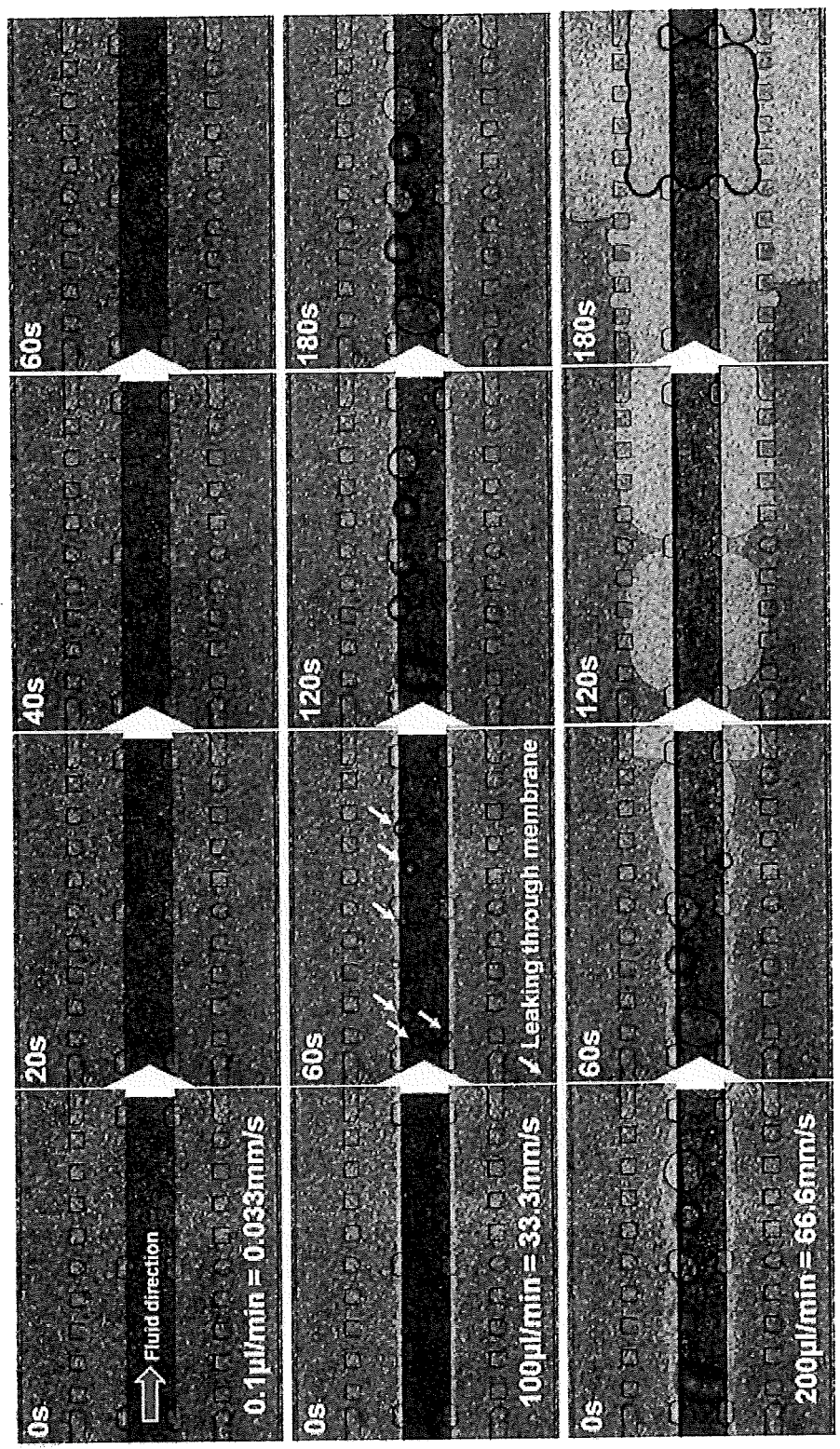
FIG. 15 depicts photographs which show fluid movement from the top channel of the incubating platform shown in FIG. 3 to the reservoir in the bottom panel of the through porous membrane simulating blood plasma movement across blood vessel wall.

FIG. 15 depicts photographs which show fluid movement from the top channel 61 to the reservoir 61 in the bottom panel 30. In particular, the photographs show diffusion of the fluid through the nano-porous membrane 70 simulating blood plasma movement across a blood vessel wall into the tumor matrix.

In other experiments, engineered tumors were crated and incubated using the system 10 disclosed herein. For instance, tumor tissues with seeding densities of MCF7 cells of $1\times10^7$ and $1\times10^8$ cells/ml were used with two different collagen contents, 3 and 6 mg/ml. After preparation of the cancer cell-laden collagen solutions at the desired cell and collagen concentrations, the tumor tissue was created and after gelation, the culture medium was filled along all the channels of the incubating platform 11. The platform was placed at 37° C. in a 5% CO2 environment using a microscope incubator stage. During and after culture, the growth and morphology of the MCF7 cells were imaged. At the same cell seeding density (i.e., $1\times10^7$ cells/ml), the MCF7 cells in the high collagen content gel (i.e., 6 mg/ml) grew much slower than their counterparts in the low collagen content gel (i.e., 3 mg/ml). In addition, the cell boundaries were still distinctive and the cells seemed to form aggregates without strong cell-cell adhesion. As the seeding density increased to $1\times10^8$ cells/ml; however, the cells seemed to form aggregates with cell-cell adhesion even at the high collagen content. At this condition, cell-driven matrix contraction was even observed in some regions. These result demonstrate the capability of the system 10 to create tumors with different cell-cell/cell-ECM adhesion characteristics and microstructures.

In another experiment, tumor spheroids were prepared to recapitulate an in vivo avasculature solid tumor. A hydrogel micro-scaffold was fabricated to provide mechanical strength for culturing suspended tumor spheroids. A PDMS template containing circular posts (3 mm in diameter; 2.5 mm in height) was used to make imprints onto the surface of gelatin (porcine origin, 40 w/v % in water) to create wells. MCF7 cell suspension ($10^6$ cells/ml) and Matrigel ECM were mixed (1:1 v/v ratio), and 15 μl of cell-ECM solution was transferred into individual wells in the gelatin hydrogel micro-scaffold. After 7 days of culturing at 37° C., tumor spheroids were extracted from the wells. The spheroids were rinsed with PBS several times prior to fixation for SEM imaging. Extracted spheroids were fixed in 4% glutaraldehyde for 2 hr, followed by secondary fixation in 1% osmium tetroxide for 2 hr. The fixed spheroids were subject to chemical dehydration in a series of ethanol solutions. Dehydrated spheroids were mounted onto an aluminum stub prior to critical point drying and then sputter-coated with gold. A scanning electron microscope (JEOL-840) was used to take micrographs. A significant morphological difference was observed between a tumor spheroid and an aggregate of MCF7 cells. MCF7 cell aggregates were formed when cells were cultured in the absence of the Matrigel ECM. Tumor spheroids cultured in the hydrogel micro-scaffold demonstrated tight cell-cell interactions in comparison to MCF7 aggregates. Individual MCF7 cells were distinctive in the SEM micrograph of aggregates whereas no discernible individual MCF7 cells were observed in the spheroid establishing rather a smooth outer surface. Thus, the system 10 disclosed herein is also suitable to create and study tumor microenvironments with highly packed cell-cell junctions in the reservoir 32, which cannot be easily mimicked on conventional microfluidics with 2D cell cultures.

In another experiment intended to verify NP transport capabilities of the system 10, fluorescent NPs simulating drugs and/or drug delivery carriers were mixed into MCF7 culture medium, and the solution flowed along the capillary channel 61. Two different sizes of fluorescent NPs were tested—(i) 500 kDa FITC-labeled dextran, whose hydrodynamic equivalent diameter is approximately 20 nm, and (ii) 100 nm fluorescent polystyrene NPs. While controlling the interstitial fluid pressure (IFP) along the tumor reservoir 32 (10 mmHg) and the capillary fluid pressure (CFP=10 mmHg), the incubating platform 11 was imaged under confocal microscopy to characterize the spatiotemporal changes of the fluorescence intensity. Time-lapse images were analyzed to determine the diffusivity of the NPs under a given tumor IFP, assuming the fluorescence intensity is proportional to the local concentration of the NPs.

In order to establish a theoretical framework for the in vivo NP transport processes, theoretical analyses were performed of the NP transport around a capillary including extravasation and interstitial transport simultaneously. The flux of extravasation was computed by the Kedem-Katchalsky formulation and then used to provide a boundary condition for the interstitial transport as follows: $-D_{eff} \partial C/\partial r + v_r C = P[C_v - C/K_{AV}]$ at $r=R_c$, where C is the NP concentration, $C_v$ is that in the capillary, $D_{eff}$ is the diffusivity, $v_r$ is the interstitial fluid velocity, P is the endothelial permeability, $K_{AV}$ is the available volume fraction of the NPs, and $R_c$ is the capillary radius. The concentration of the NPs in the capillary varies with respect to time to simulate the clearance by the RES as follows: $C_v(t) = C_i V_i \cdot k_1 \exp(-k_2 t)$, where $k_1$ and $k_2$ are the pharmokinetic constants and the subscript "i" denotes the intravenously injected quantities. Then, the interstitial transport was simulated by solving the chemical species conservation equation considering: (i) the diffusion through porous ECM; and (ii) the convection by the interstitial fluid flow caused by the elevated tumor IFP. Three different sizes of NPs were simulated –3 nm, 40 nm and 100 nm in diameter—with the relevant permeability of the endothelium, and the diffusivity of tumor tissues obtained from the literature.

Time-lapse fluorescence micrographs verified the spatiotemporal transport of the NPs when both IFP and CFP were 10 mmHg. Changes of the NP concentration were correlated to the fluorescence intensity, and the intensity profiles clearly show the spatiotemporal transport of the 500 kDa dextran. In the capillary channel 61, the fluorescence intensity rapidly increased within the first 4 hr and then decreased at 6 hr. In the tumor reservoir 32, the concentration near the channel interface increased similar to that of the capillary channel due to the extravasation of the dextran, and subsequent interstitial transport of dextran was observed. At 6 hr, when the concentration in the capillary channel decreased, the concentration near the channel interface also decreased due to less extravasation, but interstitial diffusion still occurred which resulted in a plateau in the concentration profile. The observed transport behavior of 100 nm polystyrene NPs was substantially slower than the transport of the 500 kDa dextran, which resulted in no noticeable transport during the same time period. These result demonstrate that the proposed incubating platform 11 disclosed herein can simulate complex in vivo transport processes around tumors.

In this latter experiment, although all NPs were extravasated and permeated through the tumor interstitium, the extent of the extravasation and permeation notably decreased with particle size. The NP concentration in the capillary ($r/R_c<1$) decreased with time, which simulates the clearance by the RES. The 3 nm NPs rapidly extravasate and permeate deep into the interstitium at early times, but at later times (i.e., after 8 hrs) the NPs may diffuse back into the blood stream because the NP concentration in the capillary is lower than that in the interstitium. The 40 nm and 100 nm NPs extravasate to a similar extent, but the 40 nm NPs show a notably higher interstitial penetration than the 100 nm NPs because of their higher diffusivity originating from their smaller size. Overall, the 100 nm NPs show significantly lower distribution throughout the tumor compared to the smaller NPs. Interestingly, the larger NPs extravasate longer than the 3 nm NPs (even after 8 hrs) because their less extravasation at earlier times makes the extravasation flux positive even when the capillary concentration decreases. These results suggest that the clearance by the RES is also a major factor in determining interstitial transport. The results also imply that, in addition to the size window, there is a temporal window within which the NP transport can be enhanced using concentration gradient-driven transport processes (i.e., diffusion and convection), and this time window is dependent on the size of the NPs and the clearance rate. These results confirm that the multiple levels of transport processes, including blood flow-driven transport, extravasation, and interstitial transport, should be considered simultaneously to properly design successful targeted delivery strategies. The system 10 simulates all of these conditions of the transport process. The system 10 and particularly the incubating platform 11, allows for rapid and real-time evaluation of the ability of a particular NP to penetrate a particular cellular matrix, and more particularly a 3D tumor. The same platform can be used for rapid, real-time evaluation of the drug response of an engineered tumor with a strong correlation to the drug response of the tumor in vivo.

Those skilled in the art will recognize that numerous modifications can be made to the specific implementations described above. Therefore, disclosure provided herein is not to be limited to the embodiments described herein. For instance, although the examples described herein relate to larger constructs and nanoparticles for drug delivery, the systems and methods described herein can be used for testing of all manner of drugs and drug formulations, including at the molecular level.

What is claimed is:

1. A fluidic system for performing tests on a three-dimensional (3D) cellular structure, comprising:
    a bottom panel disposed beneath said top panel, said bottom panel defining;
    a reservoir open at opposite ends for flowing a fluid therethrough and sized to contain the 3D cellular structure;
    at least one side channel flanking said reservoir and coextensive with at least a portion of a length of said reservoir, said at least one side channel open at its opposite ends for flowing a fluid therethrough; and
    a side wall between said reservoir and a corresponding one of said at least one side channel, said side wall defining openings for fluid communication between said reservoir and said corresponding side channel, said openings sized to simulate interstitial transport to and from a lymphatic vessel of a living animal;
    a top panel disposed above said bottom panel and defining a top channel open at opposite ends for flowing a fluid therethrough, said top channel at least partially coincident with said reservoir; and a porous membrane disposed between said top channel and said reservoir at least where said channels are coincident, said porous membrane having pores sized to mimic transvascular transport through the endothelium of a blood vessel of the living animal.

2. The fluidic system of claim 1, wherein the fluid is culture medium, human sera or blood.

3. The fluidic system of claim 1, further comprising:

at least one first pressure source fluidly connected to an end of said at least one side channels, each first pressure source calibrated to simulate the lymphatic pressure of the living animal;

at least one second pressure source fluidly connected to an end of said reservoir and calibrated to simulate the interstitial pressure of the living animal; and at least one third pressure source fluidly connected to said top channel and calibrated to simulate the capillary pressure of the living animal.

4. The fluidic system of claim 3, wherein:

said at least one first pressure source is configured to maintain a pressure of about 5 mmHg in said at least one side channel;

said at least one second pressure source is configured to maintain a pressure in the range of about 5 to 150 mmHg in said reservoir; and said at least one third pressure source is configured to maintain a pressure in the range of 10 to 40 mmHg in said first channel.

5. The fluidic system of claim 1, further comprising a viewing window in said reservoir.

6. The fluidic system of claim 1, wherein said membrane is coated with endothelial cells.

7. The fluidic system of claim 1, wherein said top channel is fluidly connected to a source of nanoparticles adapted for use as a carrier for drugs to treat the cells of the 3D cellular structure.

8. The fluidic system of claim 1, wherein said top channel has a width of about 300 μm and a height of about 50 μm.

9. The fluidic system of claim 1, wherein said reservoir has a width of about 900 μm and a height of about 100 μm.

10. The fluidic system of claim 1, wherein said side channels have a width of about 300 μm and a height of about 100 μm.

11. The fluidic system of claim 1, wherein said side walls are defined by a plurality of posts defining said openings therebetween.

12. The fluidic system of claim 11, wherein said posts have a width along the length of said wall of about 100 μm.

13. The fluidic system of claim 1, wherein said porous membrane has pores with an effective diameter of between 1 nm and 1000 nm.

14. The fluidic system of claim 12, further comprising a plurality of posts disposed within said reservoir.

* * * * *